United States Patent
Al-Jutaily (10) Patent No.: US 8,408,053 B2
(45) Date of Patent: Apr. 2, 2013

(54) METHOD AND APPARATUS TO EVALUATE MULTI-PHASE CORROSION INHIBITOR

(75) Inventor: Sulaiman A. Al-Jutaily, Dhahran (SA)

(73) Assignee: Saudi Arabian Oil Company (SA)

( * ) Notice: Subject to any disclaimer, the term of this patent is extended or adjusted under 35 U.S.C. 154(b) by 294 days.

(21) Appl. No.: 12/786,247

(22) Filed: May 24, 2010

(65) Prior Publication Data
US 2011/0283783 A1    Nov. 24, 2011

(51) Int. Cl.
*G01N 3/00* (2006.01)
(52) U.S. Cl. .......................................... 73/86
(58) Field of Classification Search ................ 73/86
See application file for complete search history.

(56) References Cited

U.S. PATENT DOCUMENTS

| | | | |
|---|---|---|---|
| 2,756,120 A * | 7/1956 | Lothringer | 422/8 |
| 2,786,021 A | 3/1957 | Marsh | |
| 3,228,236 A | 1/1966 | Landrum et al. | |
| 3,418,848 A | 12/1968 | Schaschl | |
| 3,491,012 A | 1/1970 | Winslow, Jr. | |
| 3,632,495 A | 1/1972 | Watson et al. | |
| 4,092,122 A | 5/1978 | Suga | |
| 4,426,618 A | 1/1984 | Ronchetti et al. | |
| 4,780,664 A | 10/1988 | Ansuini et al. | |
| 5,639,959 A | 6/1997 | Reiber | |
| 6,814,854 B2 | 11/2004 | Lewis et al. | |
| 6,936,158 B2 | 8/2005 | Nielsen et al. | |
| 7,127,959 B2 | 10/2006 | Blum et al. | |
| 8,017,203 B2 * | 9/2011 | Lyublinski et al. | 428/34.1 |
| 2004/0107769 A1 | 6/2004 | Blum et al. | |
| 2006/0264335 A1 * | 11/2006 | Penna et al. | 507/244 |
| 2009/0158827 A1 * | 6/2009 | Dermody et al. | 73/86 |
| 2010/0147056 A1 * | 6/2010 | Stolle et al. | 73/86 |
| 2011/0283783 A1 * | 11/2011 | Al-Jutaily | 73/86 |

FOREIGN PATENT DOCUMENTS

| CN | 2718566 | 8/2005 |
|---|---|---|
| CN | 2718567 | 8/2005 |

OTHER PUBLICATIONS

International Search Report (PCT/US2011/037552) mailed on Aug. 11, 2011.

* cited by examiner

*Primary Examiner* — Lisa Caputo
*Assistant Examiner* — Jamel Williams
(74) *Attorney, Agent, or Firm* — Bracewell & Giuliani LLP (57) ABSTRACT

The present invention relates to a process for measuring the effectiveness of a corrosion inhibitor. More specifically, the invention relates to placing a corrosion inhibitor in at least one fluid and then simultaneously suspending coupons in the fluid having the corrosion inhibitor and at least one additional fluid, wherein both fluids are contained in the same vessel.

22 Claims, 10 Drawing Sheets

METHOD AND APPARATUS TO EVALUATE MULTI-PHASE CORROSION INHIBITOR

BACKGROUND OF THE INVENTION

1. Field of the Invention

The present invention relates to a process for evaluating corrosion inhibitors. More specifically, the invention relates to simultaneously performing a single test of multiple samples, wherein some of the samples are located in different fluids.

2. Description of the Related Art

Corrosion is the destructive attack of a material by reaction with its environment. The serious consequences of the corrosion process have become a significant problem in various environments, including manufacturing, hydrocarbon refining, drilling for minerals, and maritime operations. Corrosion causes plant shutdowns, wasted resources, loss or contamination of product, reduction in efficiency, costly maintenance, and expensive over-design of components. Furthermore, corroded components can cause unsafe conditions.

Corrosion has a tremendous impact on equipment in refineries, drilling operations, storage facilities, chemical plants, and any other facility that handles corrosive materials. A corrosive material is a fluid containing one or more corrosive chemicals. Thus exposure to the corrosive material can cause corrosion. The effects of corrosion can be reduced by adding a corrosion inhibitor to a process stream or storage unit. The effectiveness of corrosion inhibitors can change, however, depending on the physical state of the process stream and the corrosion inhibitor. During processing, liquids such as oil and water can contain corrosive materials and can separate to form stratified layers. Furthermore, outgasing can create a gas layer in the process stream, above the liquid portion of the process stream. Corrosion inhibitors can be added to the process stream to reduce the impact of corrosive chemicals, but a corrosion inhibitor that is effective in a liquid chemical can be less effective in water than in a hydrocarbon stream, and still less effective in gas than in liquid. It is useful to test corrosion inhibitors in various liquids and gas.

A coupon can be used to test a corrosion inhibitor. A coupon is a sample of material such as metal, and can be of the same type of metal as that used for equipment or pipe in a chemical processing facility. In a typical corrosion inhibitor test, the corrosion inhibitor is added to a corrosive material. A coupon is cleaned and submerged in the corrosive material for a period of time. The coupon is then removed from the corrosive material, cleaned, and weighed again. The change in weight is an indication of the effects of corrosion. A relatively small change in weight indicates an effective corrosion inhibitor.

The simplest method of estimating corrosion rate is the weight loss technique, wherein the weight of a coupon is weighed before and after exposure to a corrosive material. To perform the weight-loss corrosion estimation, the coupon is first cleaned and weighed to determine an initial weight of the coupon. The coupon is then exposed to the corrosive material for a predetermined period of time. After the exposure, the coupon is cleaned of all corrosive material and then re-weighed to determine a final weight of the coupon. The Weight Loss of the coupon is calculated by subtracting the final weight from the initial weight. The total metal loss can be calculated as follows:

$$\text{Metal Loss} = \text{Weight Loss(g)} * K / \text{Alloy Density(g/cm}^3) * \text{Exposed Area}(A)$$

The weight loss technique is a relatively slow measurement technique. It is often used as a calibration standard for devices that estimate corrosion, such as Linear Polarization and Electrical Resistance.

Corrosive materials can exist in different states and can include various liquids that can mix and separate during processing. For example, the process stream can include both oil and water, and corrosive chemicals can be present in both the oil and the water, and the oil and water can mix together during processing. Furthermore, corrosive chemicals in the oil/water mixture can evolve as gas or vapor and be present in gaseous form during processing. Outgassing is the slow release of a gas that was trapped, absorbed, adsorbed, or the like, in some material. It can also be the product of slow chemical reactions. Outgassing can also be used as a method to remove embedded gases, typically by heating or reducing of pressure. Various components used in manufacturing, refining, transporting, storing, or processing of oil or chemicals can be simultaneously exposed to corrosive chemicals in various forms. Some corrosion inhibitors can be suitable for protecting against such multiphase corrosion. Conventional corrosion testing only evaluates the effectiveness of one phase of a corrosive material at a time. Thus to test three phases of a corrosive material requires three separate tests which may inadequately simulate the distribution of corrosion inhibitor in any specific fluid or phase. Furthermore, performing separate tests may overlook the evolution of gases from a liquid, or the transfer of corrosive chemicals between oil and water phases that occurs in the process stream. Finally, it is time consuming to independently test each of several phases.

Therefore, improved methods for testing the effectiveness of multiphase corrosion inhibitors is needed. Specifically, a test that simultaneously exposes a material to several phases in a manner that simulates the interaction between phases that occurs in the process stream during actual operations is needed.

SUMMARY OF THE INVENTION

A test that simultaneously exposes a material to fluids in a manner that simulates the interaction between phases can be performed by an apparatus for measuring the effects of corrosion.

In an exemplary embodiment, an apparatus for measuring the effects of corrosion includes a container having a top, and the container is adapted to receive a first fluid and a second fluid within the container. A shaft is suspended from the top and extends into the container. The shaft is adapted to receive a first coupon and a second coupon, and to place the first coupon into contact with the first fluid and to place the second coupon into contact with the second fluid. The exemplary embodiment also has at least one sealing ring located adjacent to the first coupon and at least one sealing ring located adjacent to the second coupon, wherein the sealing rings prevent at least part of each coupon from contacting the first or second fluid.

In another embodiment, the apparatus, the container is further adapted to receive a third fluid located within the container. Also, the shaft is further adapted to receive a third coupon and place the third coupon into contact with the third fluid and at least one sealing ring is located adjacent to each coupon.

Another embodiment uses a first holder assembly, a second holder assembly, and a third holder assembly, each holder assembly having a cylindrical body and a bore, wherein the shaft passes through each of the bores of the holder assemblies. Each holder assembly is adapted to hold at least three cylindrically shaped coupons. The first holder assembly is adapted to be substantially located in the first fluid, the first fluid creating a first phase, the second holder assembly is adapted to be substantially located in the second fluid, the second fluid creating a second phase, and the third holder assembly is adapted to be substantially located in the third fluid, the third fluid creating a third phase.

In another embodiment, the apparatus includes a motor attached to the shaft, operable to rotate the shaft. In still another embodiment, the apparatus includes a first fluid and a second fluid, the first fluid creating a first phase and the second fluid creating a second phase. This embodiment also includes a plurality of holder assemblies, wherein each of the holder assemblies is adapted to hold a plurality of coupons in a different phase. In another variation of this embodiment, each of the plurality of holder assemblies is operable to be placed into a different fluid.

In another embodiment, a third fluid is located in the container, and the third fluid creates a third fluid condition. Also, the shaft is further adapted to receive a third coupon and place the third coupon into contact with the third fluid. The first fluid, second fluid, and third fluid are each oil, water, gas, or emulsions and mixtures of the same. Furthermore, at least one of the first phase, second phase, or third phase includes a corrosion inhibitor.

In an exemplary embodiment, the effects of corrosion can be measured by a method that involves weighing a first and second coupon of a first set of coupons to determine an initial first coupon weight and an initial second coupon weight, recording the initial first coupon weight and the initial second coupon weight, supporting the first coupon from the first set of coupons on a shaft, supporting the second coupon from the first set of coupons on a the shaft, placing a first fluid and a second fluid in a vessel, the first fluid creating a first phase and the second fluid creating a second phase, adding a corrosion inhibitor to at least the first phase, placing the shaft in the vessel such that the first coupon is located in the first fluid and the second coupon is located in the second fluid, maintaining the first coupon within the first fluid for a predetermined period of time, maintaining the second coupon within the second fluid for the predetermined period of time, removing the first coupon and the second coupon from the shaft after the predetermined amount of time has lapsed, weighing the first and second coupons to determine a final first coupon weight and a final second coupon weight, recording the final first coupon weight and the final second coupon weight, determining the amount of material removed by corrosion from the first coupon by comparing the final first coupon weight with the initial first coupon weight, and then determining the amount of material removed by corrosion from the second coupon by comparing the final second coupon weight with the initial second coupon weight.

In another embodiment, a first holder assembly is removably attached to the shaft and used to support the first coupon on the shaft and a second holder assembly is removably attached to the shaft and used to support the second coupon on the shaft.

In one embodiment, the vessel is pressurized during a substantial portion of the predetermined amount of time. In another embodiment, the shaft is rotated while the first and second coupons are in contact with the first and second fluid during at least a portion of the predetermined amount of time.

Still another embodiment involves installing at least one of the coupons from the first set of coupons on a third holder, attaching the third holder to the shaft, and maintaining the holder in contact with a third fluid in the vessel during the predetermined amount of time, the third fluid creating a third phase.

One embodiment includes weighing a fourth coupon, a fifth coupon, and a sixth coupon of a second set of coupons to determine an initial fourth coupon weight, an initial fifth coupon weight, and an initial sixth coupon weight, and attaching at least one coupon of the second set of coupons to each of the first, second, and third holders. In one embodiment, the method involves adding a corrosion inhibitor to at least the first phase.

In one embodiment, the first fluid is selected from the group consisting essentially of oil, water, gas, and emulsions and mixtures of the same. In another embodiment, the method includes placing at least one sealing ring adjacent to each of the coupons such that at least part of each coupon does not contact fluid. In still another embodiment, the first and second holders are separated by at least one spacer, the spacer being adapted to locate the first holder substantially in the first fluid and the second holder substantially in the second fluid for the predetermined amount of time.

In an exemplary embodiment, the apparatus for measuring the effects of corrosion includes a vessel that has a body and a lid. A shaft can be suspended from the lid and thus located within the vessel body. A first fluid and a second fluid can located within the vessel body.

An exemplary embodiment uses a first and second holder and each holder can have a bore. The shaft can pass through the first holder bore and the second holder bore, such that the first holder and second holder are removably connected to the shaft. A spacer can be located between the first and second holder to maintain the first holder a predetermined distance away from the second holder. In an exemplary embodiment, a first and second coupon can be removably attached to the first holder and placed in contact with the first fluid, and a third and fourth coupon can be removably attached to the second holder and placed in contact with the second fluid. In an exemplary embodiment, at least one sealing ring can be located between the first and second coupon, wherein the sealing ring prevents at least part of each coupon from contacting the first fluid.

In an exemplary embodiment, each coupon can be further defined by a first and second sidewall, and each sidewall of each coupon can be substantially prevented from contacting fluid. In an exemplary embodiment, a motor can be located on the lid and be operable to rotate the shaft.

In an exemplary embodiment, the apparatus also has a third fluid, and a fifth and sixth coupon located on a third holder and in contact with the third fluid. In some embodiments, the first coupon and second coupon can be made of different materials.

BRIEF DESCRIPTION OF THE DRAWINGS

So that the manner in which the above-recited features, aspects and advantages of the invention, as well as others that will become apparent, are attained and can be understood in detail, more particular description of the invention briefly summarized above may be had by reference to the embodiments thereof that are illustrated in the drawings that form a part of this specification. It is to be noted, however, that the appended drawings illustrate only preferred embodiments of the invention and are, therefore, not to be considered limiting of the invention's scope, for the invention may admit to other equally effective embodiments.

DETAILED DESCRIPTION OF THE EXEMPLARY EMBODIMENTS

Figure 1:
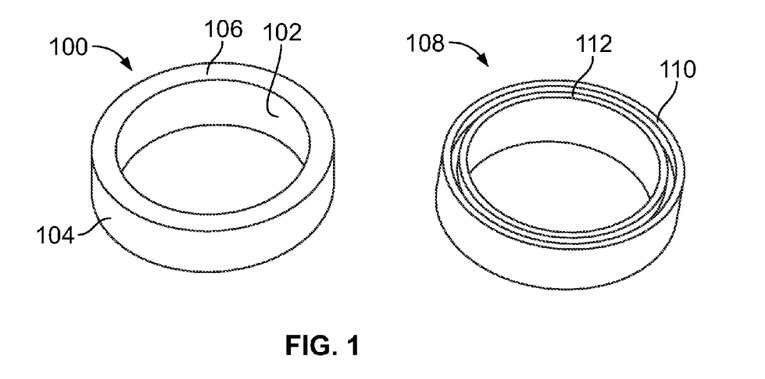
FIG. 1 shows one preferred embodiment of a coupon and a sealing ring for an apparatus to evaluate corrosion inhibitors.

Referring to FIG. 1, coupon 100 is a sample of material to be used for a corrosion resistance test. In an exemplary embodiment, the material to be tested is carbon steel (1018). The material could be steel, iron, alloy, plastic, aluminum, or any other type of material. A plurality of coupons 100 can be used in a single test and can all be made of the same material and have identical treatments (or lack thereof). Alternatively, dissimilar coupons 100 can be used in a single corrosion inhibitor test. The dissimilar coupons 100 can, for example, be different alloys or can be treated with different coatings. In a preferred embodiment, coupons 100 represent materials used in the facility for which the corrosion inhibitor is being tested. Coupons 100 could be samples of materials used, for example, in various pipes, vessels, tanks, reactors, and the like. The corrosion inhibitor to be tested can be an additive to the fluid, in which case each of the coupons to be tested can be made of the same material as each of the other coupons 100 to be tested in the single corrosion inhibitor test. In an exemplary embodiment, the coupon 100 is a cylinder or annular ring, having a bore defined by inner diameter 102, outer diameter 104, and two side-walls 106. Side-walls 106 can be substantially flat or can have an annular groove.

Sealing ring 108 is a seal that can be used to separate two adjacent coupons 100. Sealing ring 108 can be made of a chemically resistant thermoplastic, such as, for example, PolyEther-Ether-Ketone ("PEEK"), PolyPhenylene Sulfide ("PPS"), or any other material that is resistant to corrosive chemicals. Each sealing ring 108 is generally shaped to cover side-walls 106 of coupons 100. In an exemplary embodiment, wherein coupon 100 has a cylindrical shape, sealing ring 108 also has a cylindrical shape. Sealing ring 108, like coupon 100, can have other shapes. In some embodiments, sealing ring 108 has sealing ring groove 110 for receiving O-ring 112. O-ring 112 can be made of a chemically resistant elastomer material, such as Viton, Kalrez, and the like.

Holder assembly 114 (FIG. 2) holds one or more coupons 100 and sealing rings 108. In an exemplary embodiment, holder assembly 114 comprises outer holder 116 and inner holder 118 (FIG. 3). Inner holder 118 and outer holder 116 can be made of plastic, ceramic, metal, or any other material. Preferably, holder assembly 114 is resistant to corrosive materials. In an exemplary embodiment, the inner and outer holders 116, 118 are made of PEEK.

Figure 2:
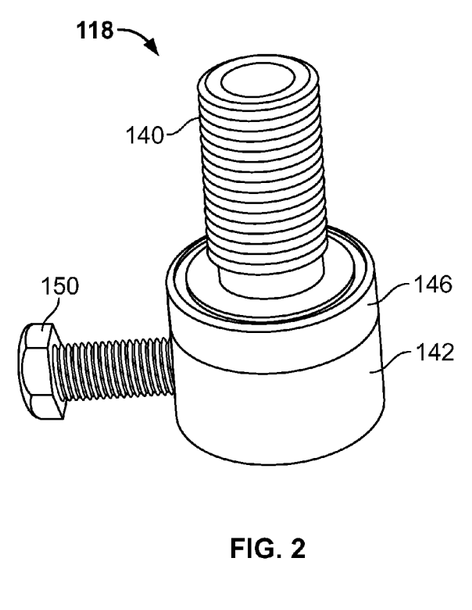
FIG. 2 shows an exemplary embodiment of an outer holder for holding the coupons and sealing rings of FIG. 1.
Figure 3:
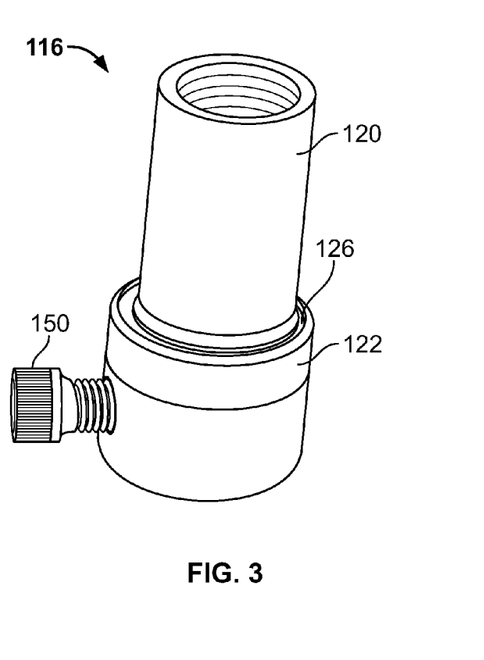
FIG. 3 shows an exemplary embodiment of an inner holder for retaining the coupons and sealing rings of FIG. 1 on the outer holder of FIG. 2.
Figure 4:
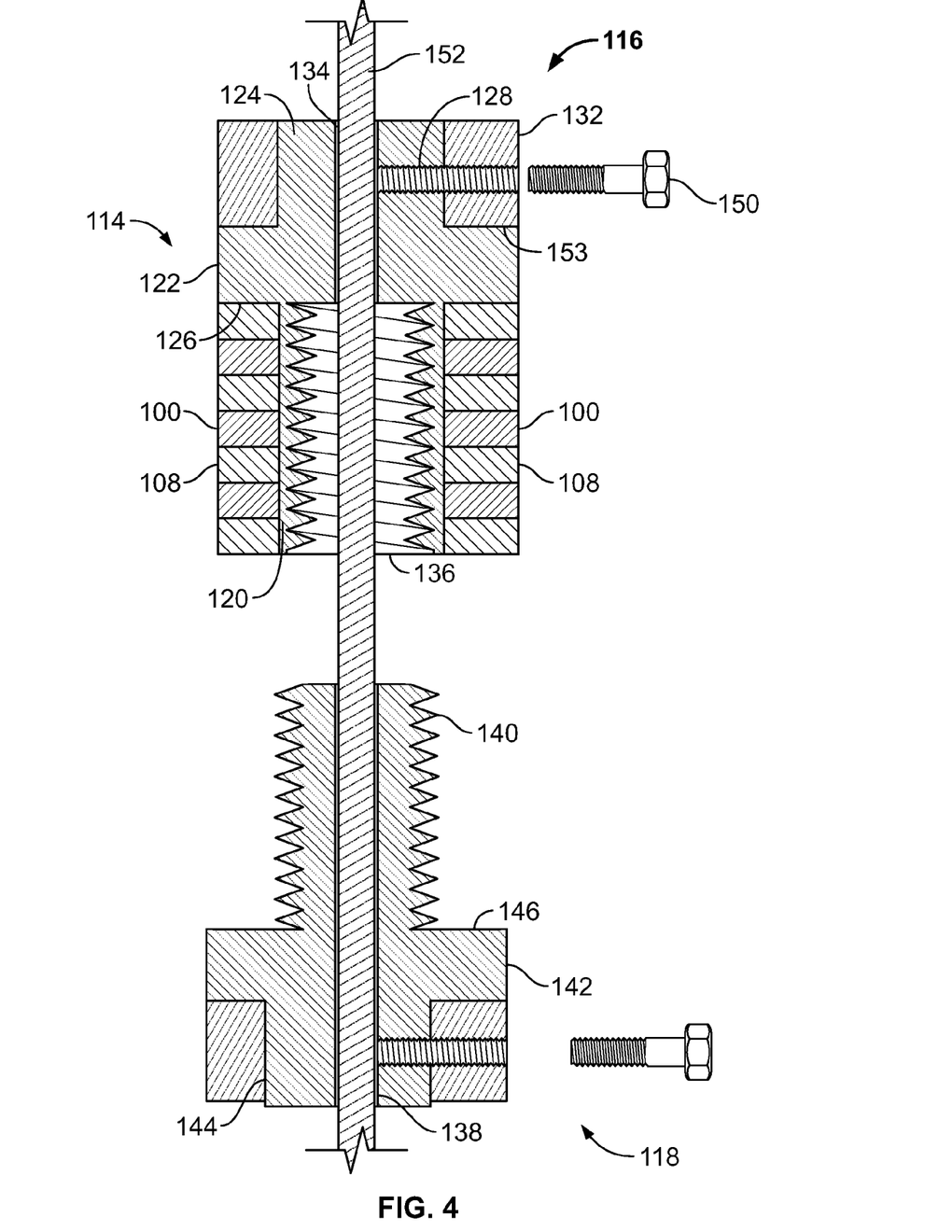
FIG. 4 shows a sectional view of an exemplary embodiment of a holder assembly for holding coupons of FIG. 1.

Referring to FIGS. 2 through 4, outer holder 116 is a cylinder rotated about an axis that comprises three cylindrical segments—coupon cylinder 120, stop ring 122, and end ring 124. The outer diameter of the coupon cylinder 120 is slightly smaller than the inner diameter of both coupon 100 and sealing ring 108. Coupon cylinder 120 has an axial length that is sufficient to hold a predetermined number of coupons 100 and sealing rings 108. In an exemplary embodiment, coupon cylinder 120 is sized to hold three coupons 100 and two sealing rings 108.

Stop ring 122 has an OD that is similar in size to the OD of coupon 100 and sealing ring 108. Stop ring 122 and outer holder 116 can be a single piece of material, or stop ring 122 can be a separate piece of material. In some embodiments, stop ring 122 has groove 126 for receiving o-ring 112 to form a seal between stop ring 122 and an adjacent coupon 100. End ring 124 is a cylinder having a smooth OD and set-screw hole 128. In a preferred embodiment, set-screw hole 128 is not threaded. In some embodiments, set-screw hole 128 can have threads. End ring 124 is sized to hold lock ring 132. Lock ring 132 will be described in more detail, below.

Outer holder 116 has threaded bore 134, wherein the inner diameter surface of threaded bore 134 includes threads 136 for engaging inner holder 118. Inner holder 118 is a cylinder rotated about an axis, having an axial bore 138, that also comprises three cylindrical segments—threaded OD 140, stop ring 142, and end ring 144. Threaded OD 140 has threads and an outer diameter sized to mate with the threads 136 of threaded bore 134. The axial length of threaded OD 140 is the same as or slightly shorter than the axial length of threaded bore 134 of coupon cylinder 120. Stop ring 142 can have a groove 146 for o-ring 112 and generally has an outer diameter similar to the outer diameter of coupons 100. End ring 144 can be similar in size to the size of end ring 124 of outer holder 116. Bore 138 of inner holder 118 can be a smooth-surface cylindrical opening running the length of the inner holder 118.

In an exemplary embodiment, coupons 100 and sealing rings 108 are alternatingly placed on coupon cylinder 120 of outer holder 116. O-ring 112 is placed first, in groove 126 of stop ring 122, followed by coupon 100, another o-ring 112, followed by sealing ring 108, then another o-ring 112 and another coupon 100, and so on until the desired number of coupons 100 are on the outer holder 116 and the combined axial length of coupons 100 and sealing members 108 equals or exceeds the axial length of coupon cylinder 120. In some embodiments, sealing rings 108 are placed between coupons 100 so that no coupon 100 contacts an adjacent coupon 100. Multiple sealing rings 108, however, can be stacked together (and in contact with adjacent sealing rings 108) until the desired axial length is achieved. In a preferred embodiment, o-ring 112 is placed adjacent to each sealing ring.

After stacking coupons 100 and sealing rings 108 on coupon cylinder 120, threaded bore 140 of the inner holder 118 is inserted into threaded bore 134 of outer cylinder 116. Inner holder 118 is tightened until the side walls of each of the stop rings 122, 142, coupons 100, and sealing rings 108 exert pressure on adjacent coupons 100 and sealing rings 108. In embodiments using an o-ring 112, the pressure is sufficient to squeeze the o-ring 112 and thus form a seal between each adjacent member. When inner holder 118 is sufficiently tight, o-rings 112, sealing rings 108, and stop rings 142 prevent fluid from contacting side-walls 106 of coupons 100 when holder assembly 114 is submerged in liquid. In some embodiments, sealing rings 108, coupons 100, and stop rings 122, 142 form a continuous seal, thus preventing fluid from reaching ID 102 of coupons 100.

Lock ring 132 is an annular ring rotated about an axis. Set-screw 150 is used with lock ring 132 to hold holder assembly 114 in place on shaft 152. Set-screw 150 may be any type of threaded screw or bolt, such as an allen-head screw, hex-head bolt, Philips-head screw, and the like. Lock ring 132 can be made out of any material having sufficient strength to hold set-screw 150 and support one or more holder assemblies 114 on shaft 152. In a preferred embodiment, lock ring 132 is made of stainless steel. One or more set-screw holes 153 are radially directed through the side of the lock ring 132. Set-screw holes 153 have threads for engaging set-screw 150. Set-screw 150 screws into set-screw hole 153, passes through set-screw hole 128 of end ring 128, and presses against shaft 152.

Figure 5:
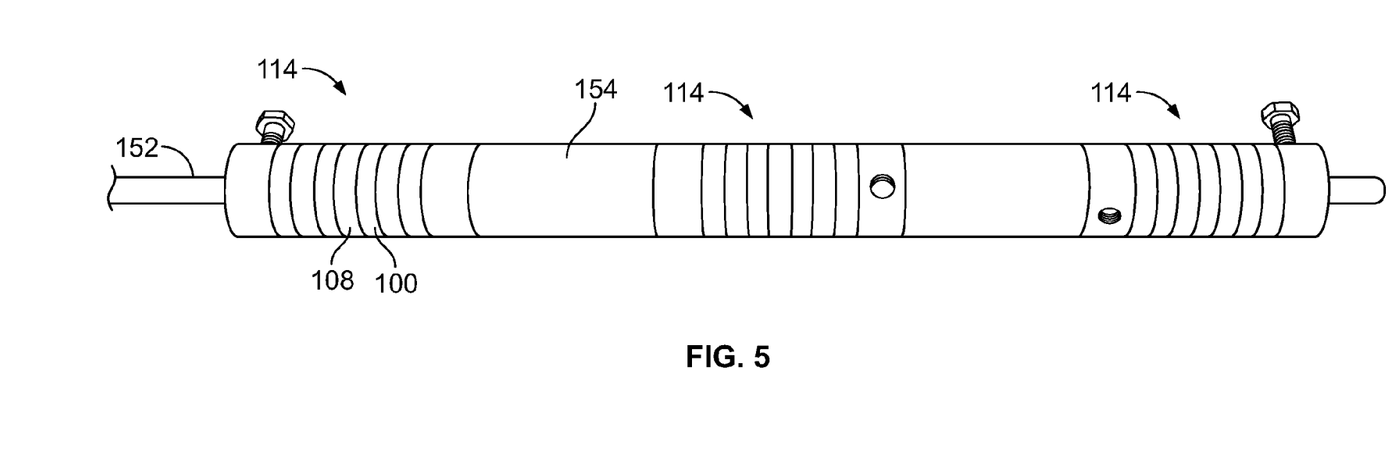
FIG. 5 shows a side view of an exemplary embodiment of a carrier with multiple holders for holding coupons of FIG. 1.

Referring to FIG. 5, shaft 152 is a rod that is sized to support holder assemblies 114. The OD of the shaft 152 is slightly smaller than the ID of bore 138 of inner holder 118. In an exemplary embodiment, shaft 152 is a 5/16" diameter Hastelloy autoclave shaft having a smooth exterior surface. Shaft 152 can be made of any suitable corrosion resistant material and can be any diameter and length.

Referring to FIG. 5, multiple holder assemblies 114, with coupons 100 and sealing rings 108, can be located on a single shaft 152 by passing the shaft 142 through bore 138 of holder assembly 114. Holder assemblies 114 can be separated from each other by spacer 154. Spacer 154 is a cylinder rotated about an axis. The bore of spacer 154 is sized to slide along shaft 152. The OD of spacer 154 is roughly the same as the outer diameters of coupons 100, sealing rings 108, and lock rings 132. Spacer 154 can be made of the same material as sealing rings 108 such as, for example, PEEK. In some embodiments (not shown), holders may be permanently attached to shaft 152 or may be integrally formed as a part of shaft 152. In some embodiments, coupons 100 may be placed on shaft 152 without the use of holders.

Figure 6:
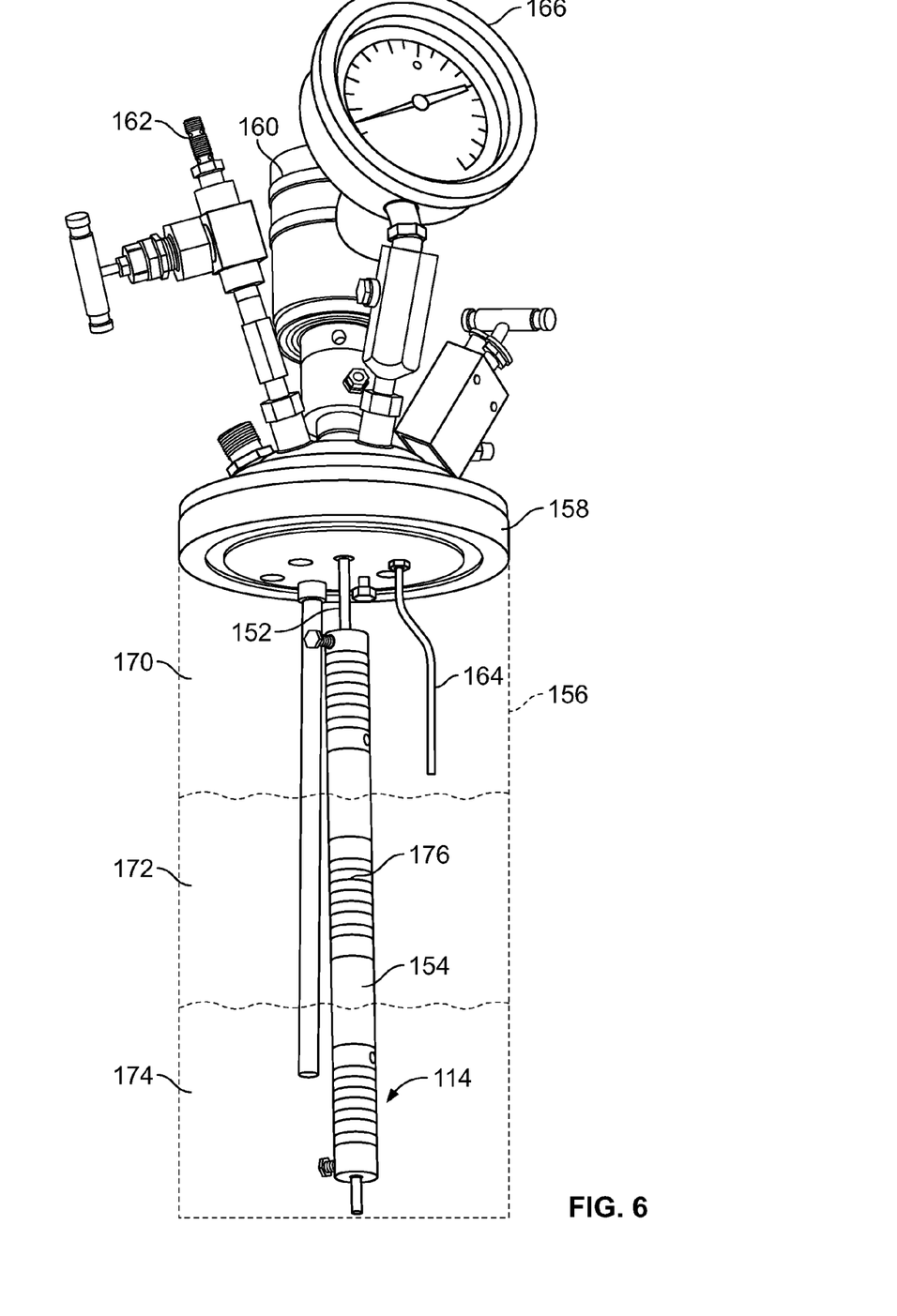
FIG. 6 shows an exemplary embodiment of an apparatus for testing multiple coupons of FIG. 1.

Referring to FIG. 6, vessel 156 is used to contain the corrosive material and shaft 152 having holders 114 with coupons 100. Shaft 152 can be suspended from lid 158 of vessel 156 or, alternatively, shaft 152 can be attached to motor 160 for rotating shaft 152. The term "attached to the motor" includes either permanently attaching shaft 152 to motor 160 or removably attaching shaft 152 to motor 160. In some embodiments, vessel 156 is an autoclave, wherein pressure, temperature, or both pressure and temperature can be elevated and, in some embodiments, controlled during corrosion testing. As one skilled in the art will appreciate, various components can be attached to lid 158 or vessel 156, including, for example, gas or liquid inlet 162, temperature probe 164, and pressure gage 168.

Vessel 156 can be filled with one or more fluids such as gas 170, oil 172, and water 174. Some fluids can separate and form layers and thus fluids 170, 172, and 174 can separate to form three distinct layers. The middle layer can include, for example, oil 172, which will likely float on top of water 174, which could be, for example, included in the third layer. A layer of gas 170 can be present above the liquid or liquids. Thus three different fluids can be present in a single vessel 156. More or fewer fluids can be present and the type of fluids is not limited to oil, water, or gases. In a preferred embodiment, there is at least some stratification between layers of fluids. Some mixing or cross contamination between the layers, however, can be desirable for the sake of simulating conditions of actual corrosive chemicals and corrosion inhibitors.

A corrosion inhibitor can be added to one or more of the fluids in vessel 156. When the corrosion inhibitor is present in one or more of the liquid fluids, such as, for example oil 172 or water 174, it can outgas and thus offer a degree of corrosion protection in the gas layer. The effectiveness of the corrosion inhibitor can be different depending on the particular fluid in which the corrosion inhibitor is present. Thus, a different corrosion inhibitor condition can exist for each of the different fluid types in which a corrosion inhibitor can be present. A corrosion inhibitor condition can also include a situation wherein a fluid type or combination of fluid types result in no corrosion inhibitor being present in a particular fluid.

Each fluid can define a different phase. For example, phases can be liquid or vapor. In one embodiment, a liquid phase is a hydrocarbon, another phase is aqueous, and still another phase is a vapor. Furthermore, a fluid that is predominantly one type of liquid can define a phase regardless of whether other fluids may be present in addition to the predominant fluid. Indeed, in one embodiment, fluids can mix with adjacent fluids, and thus a phase can include an emulsion of two or more fluids. One or more phases can include a corrosion inhibitor. The corrosion inhibitor can be added directly to the phase or the corrosion inhibitor can be added to a different phase and then migrate between phases. Corrosion inhibitors can be added to the fluid in vessel 156 or added to the fluid before the fluid is placed in the vessel 156. Any concentration of corrosion inhibitor can be tested. In a preferred embodiment, the corrosion inhibitor concentration is 25 parts per million ("ppm").

In an exemplary embodiment, shaft 152 having multiple holder assemblies is placed in vessel 156. Holder assembly 114 is located near the bottom of shaft 152, thus exposing the lower set of coupons 100 to a bottom-most fluid, such as 174. A first spacer 154 is used to cause the second holder assembly 114 to be located in a second layer of fluid, such as oil 172, and above the bottom-most fluid. A second spacer 154 above second holder assembly 114 causes a third holder assembly 114 to be located in a third layer of fluid, such as gas 170. Thus each set of coupons 100 is exposed to a different fluid.

In some embodiments, coupons 100 having different properties can be tested. If three different coupon materials are to be tested, each holder assembly 114 can have one of each of the three different types of coupons 100. In embodiments having, for example, three different fluids 170, 172, 174 and three different types of coupons 100, nine coupons would be used. Each coupon 100 type is exposed to each fluid type during a single test. In embodiments using a single coupon 100 type, three samples of the single coupon type can be placed on each of three holder assemblies. Corrosive effects 176 may occur on the surfaces of coupons 100 during testing.

In some embodiments, a motor 160 spins shaft 152 while coupons 100 are exposed to the various fluids. Shaft 152, and thus holder assemblies 114, can spin slowly, thus causing little agitation within the fluids, or it can spin more rapidly, thus causing greater mixing between fluids. The rotating shaft 152 can also increase the rate at which corrosive chemicals or corrosion inhibitors outgas into gas layer 170. Shaft 152 can spin at any rate. Preferably, the rotation speed is less than 1000 RPM to avoid creating a vortex within the fluids. In a preferred embodiment, shaft 152 spins at 500 revolutions per minute.

Referring to FIG. 7, to test a corrosion inhibitor, a technician first obtains or creates coupons (step 202). The coupons can all be identical, or they can be different materials. The technician cleans the coupons in step 204. One of skill in the art will appreciate both the methods and the importance of cleaning a coupon prior to weighing it. The coupons are weighed individually in step 206 to determine an initial coupon weight for each coupon. The weight of the coupons can be recorded in any of a variety of ways including, for example, hand-writing, entry into a computer, or within the memory of the scale on which the coupons are weighed. With the coupons cleaned and weighed, the technician assembles each of the holder assemblies by first sliding an o-ring onto an outer holder coupon cylinder and aligning the o-ring with the groove on the stop ring. The technician next slides the first coupon onto the coupon cylinder of the outer holder assembly (step 208), then slides a second o-ring onto the coupon cylinder in step 209. In step 210, the operator slides a sealing ring onto the coupon cylinder, ensuring that the previously installed o-ring lines up with the groove in the sealing ring. The process is repeated for additional o-rings, coupons, and sealing rings in steps 211-217.

Figure 7A:
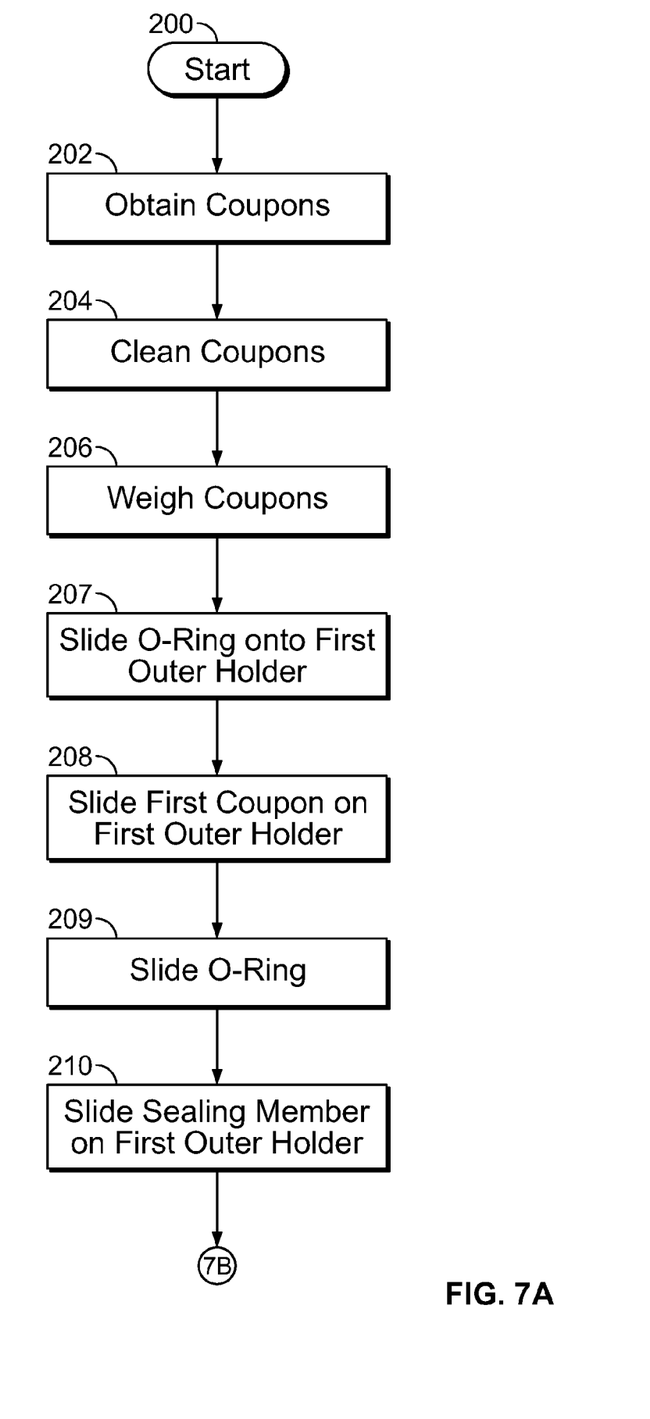
FIG. 7 shows a flow diagram for an exemplary embodiment of a method for testing multiple coupons of FIG. 1.
Figure 7B:
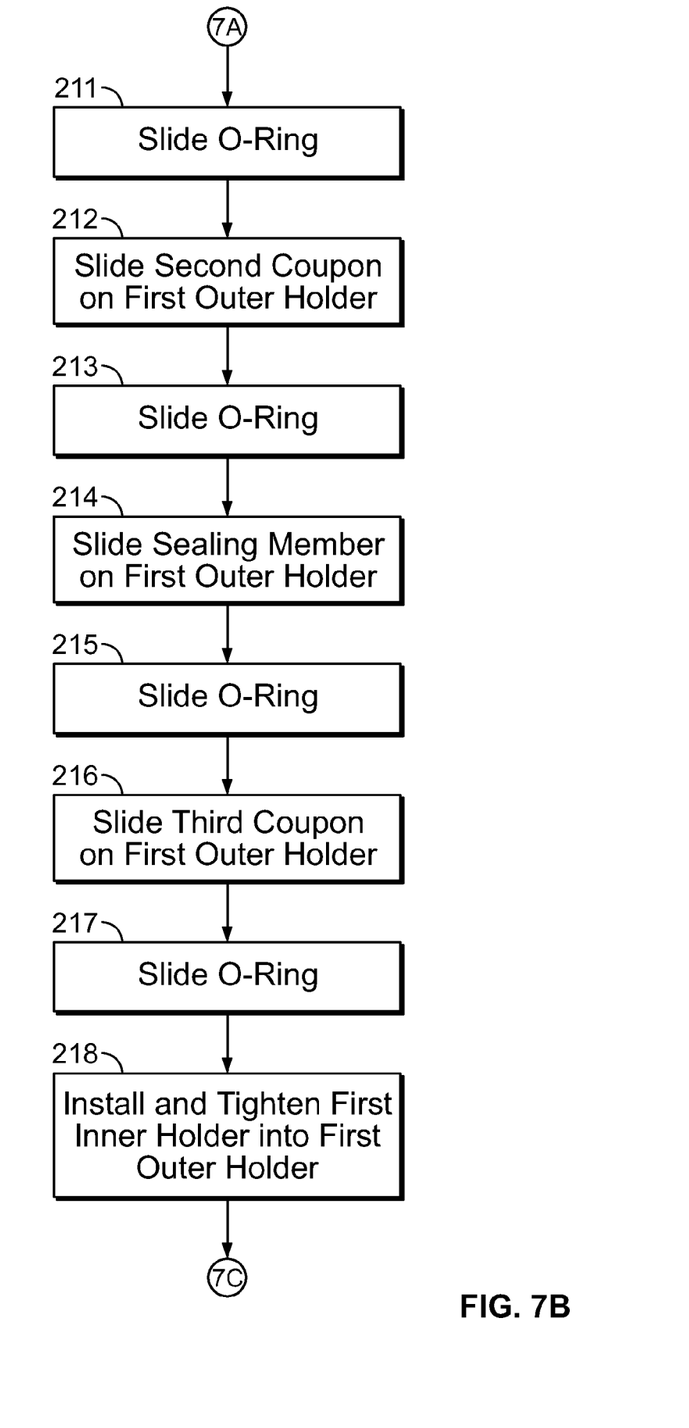
Figure 7C:
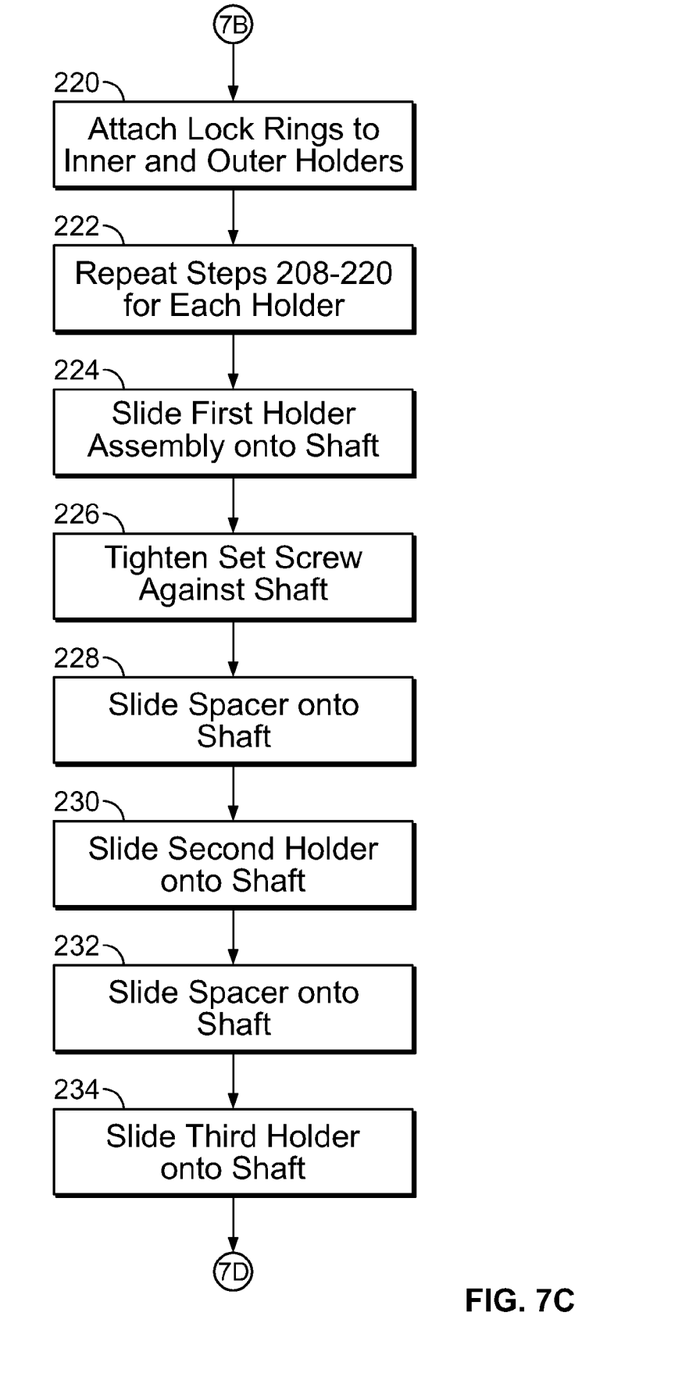

The technician next inserts the threaded shaft of the inner holder into the threaded bore of the outer holder and tightens the shaft in step 218. The technician ensures that the two components are tight enough to maintain pressure on all of the o-rings and thus form a seal between each of the components. In step 220, the technician slides lock rings onto the ends of the holder assembly. In step 222, the technician repeats steps 208 through 220 for each of the required holder assemblies.

Figure 7D:
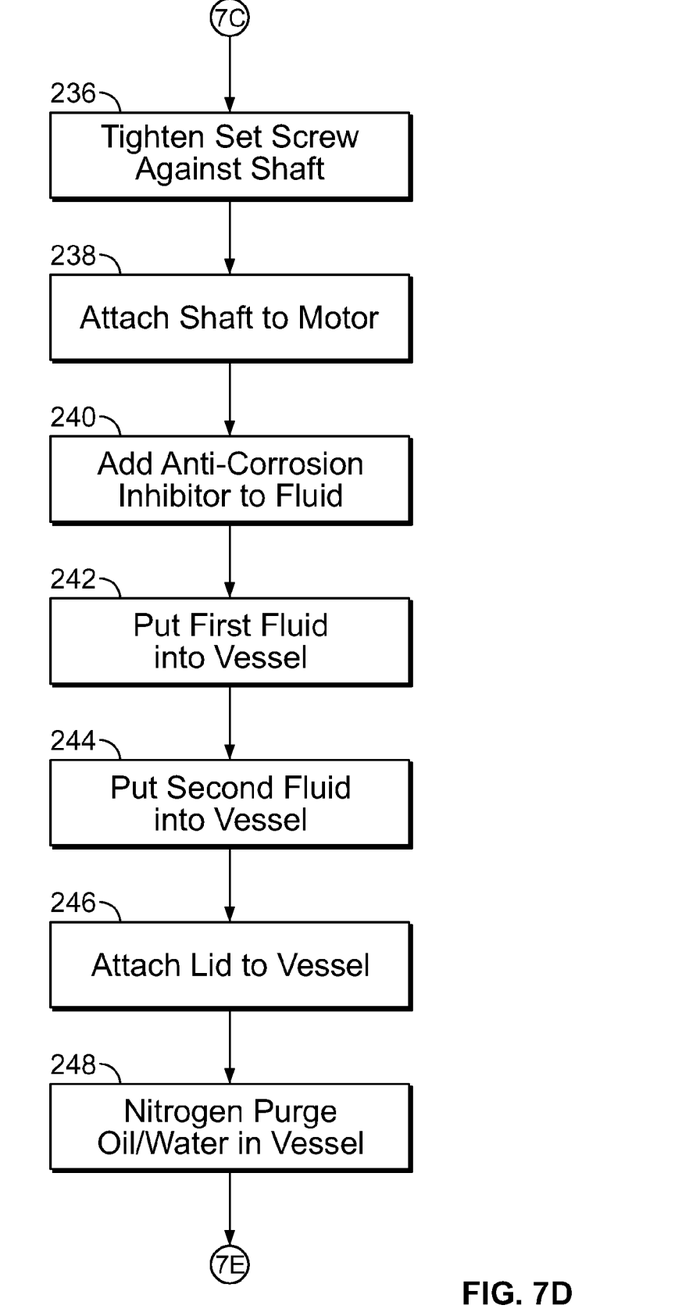

The technician inserts the shaft through the bore of a completed holder assembly in step 224. The technician tightens the set-screw against the shaft, thus locking the holder assembly in place in step 226. The technician slides a spacer onto the shaft in step 228. The technician slides a second holder assembly and then a spacer onto the shaft in steps 230-232. A third holder is placed on the shaft in step 234 and then a set-screw is used to secure the third holder to the shaft in step 236. The technician can exert force against the holders to compress the holders together prior to tightening the set-screw, thus forming a seal between the spacers and holder assemblies. The completed shaft assembly is shown in FIG. 5. The technician can attach the shaft to a motor, wherein the motor is mounted to the lid of a vessel, in step 238.

Figure 7E:
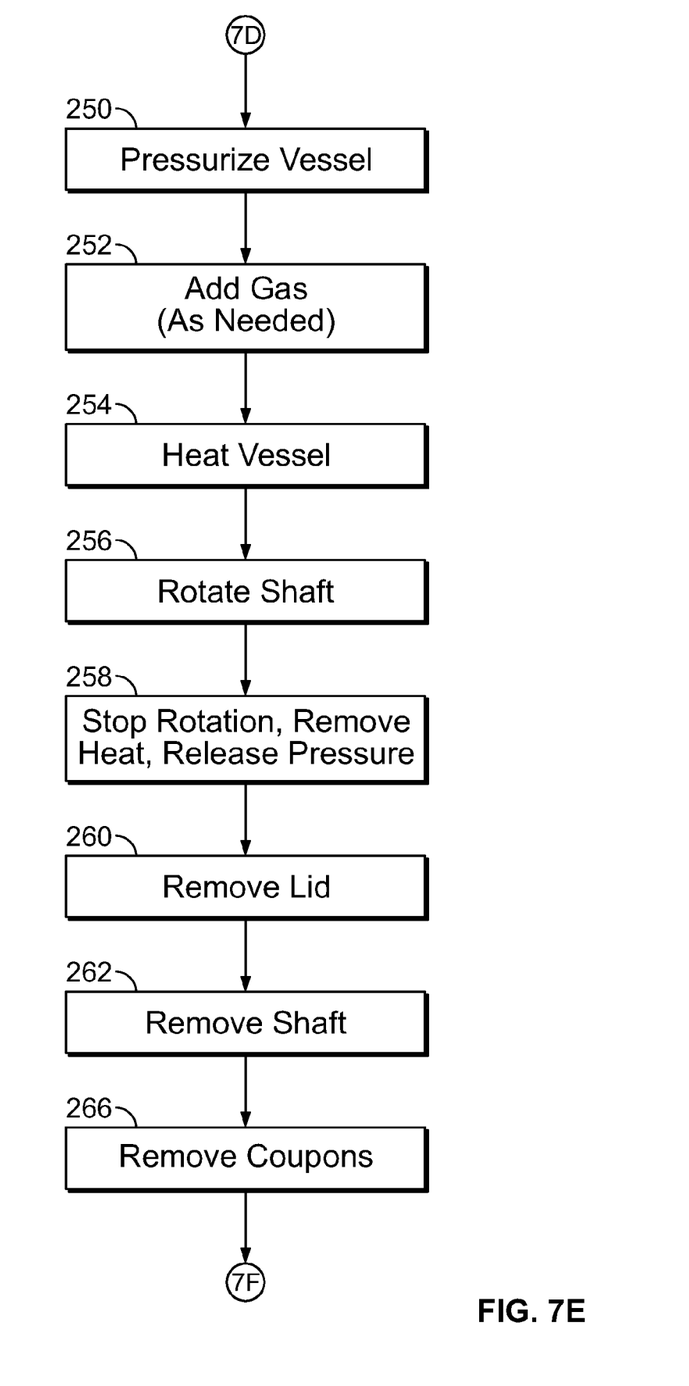

To prepare the vessel, the technician adds the corrosion inhibitor to be tested to one or more of the fluids in step 240. The corrosion inhibitor can be added to the fluids after the fluid or fluids are placed in the vessel. The first and second fluids are placed in the vessel in steps 242-244. The lid, with the shaft in place, is attached to the vessel in step 246. If a nitrogen purge of the fluids is desired, the nitrogen purge is performed in step 248. The technician can pressurize the vessel in step 250. If any additional gas is required to test a gaseous fluid, the gas can be added in step 252. If the corrosion inhibitor test is requires heat, the fluid in the vessel is heated in step 254.

The technician then rotates the shaft to cause the coupons to rotate in the fluid in step 256. The rotation period can be any time, from a few minutes to days. If rotation is not required, the coupons simply remain located in relatively static contact with static fluid. After the reaction time is complete, the technician stops the rotation, removes the heat source, and releases pressure in the vessel (as needed) in step 258.

Figure 7F:
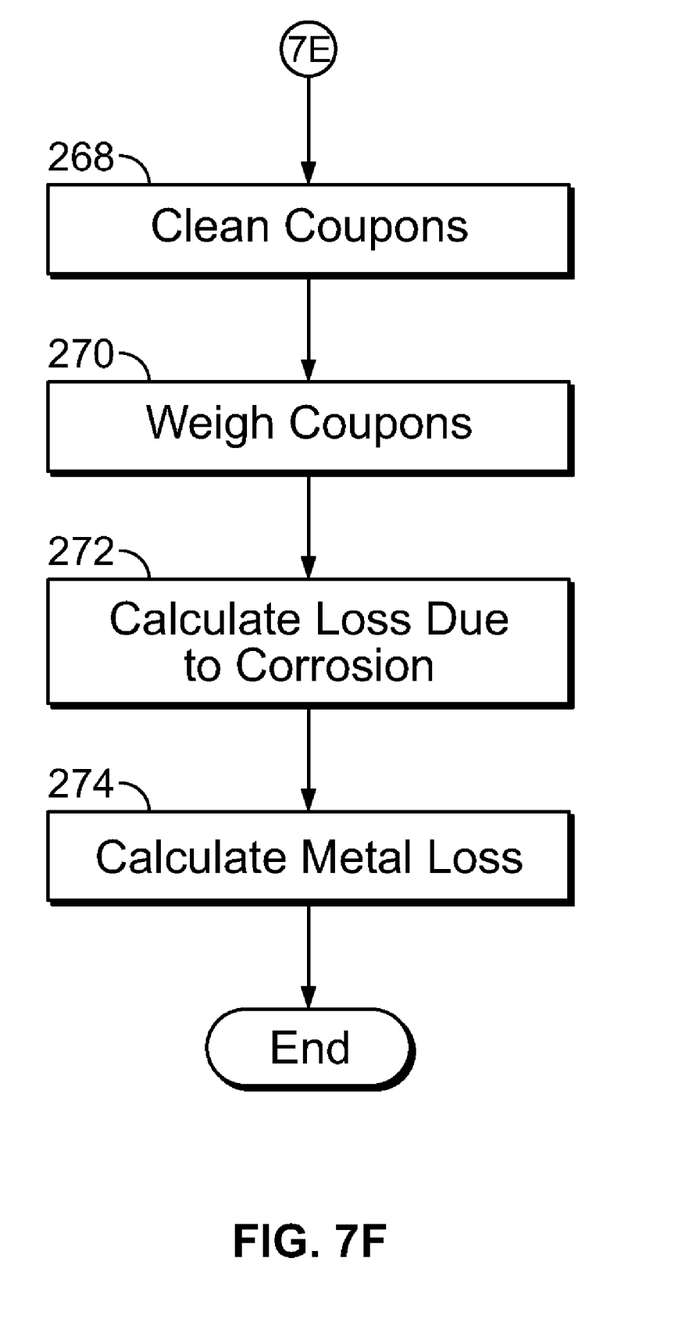

Finally, the lid is removed, the shaft is removed from the lid, and the shaft and holder assemblies are disassembled in steps 260-266. The technician is careful to identify each coupon as the coupon is removed. The technician then cleans each coupon (step 268) and weighs each coupon (step 270) to determine a final weight of each coupon. The initial and final weight of each coupon is compared in step 272. The comparison may be done in any of a variety of ways. For example, the final weight may be recorded in a manner similar to the manner in which the initial weight was recorded and then compared by substraction. Similarly, if the initial weight was recorded in a computer such as personal computer or the memory of the scale used to weigh the samples, the computer may compare the initial and final weights on the coupons. Finally, the corrosion Metal Loss is calculated in step 274 based on the change in weight.

Although the detailed description contains many specific details for purposes of illustration, one of ordinary skill in the art will appreciate that many variations and alterations to the details are within the scope and spirit of the invention. Accordingly, the exemplary embodiments of the invention described herein are set forth without any loss of generality to, and without imposing limitations thereon, the present invention.

As used herein, optional or optionally means that the subsequently described event or circumstances may or may not occur. The description includes instances where the event or circumstance occurs and instances where it does not occur.

As used herein, recitation of the term about and approximately with respect to a range of values should be interpreted to include both the upper and lower end of the recited range. Ranges may be expressed herein as from about one particular value, and/or to about another particular value. When such a range is expressed, it is to be understood that another embodiment is from the one particular value and/or to the other particular value, along with all combinations within said range.

As used in the specification and claims, the singular form "a", "an" and "the" may include plural references, unless the context clearly dictates the singular form. The descriptive references such as "first," "second," and "third" are intended to provide clarity in this specification. The "first," "second," and "third" monikers are not intended to define a particular position or location and thus the descriptive reference in the specification should not be considered a limiting reference.

Throughout this application, where patents or publications are referenced, the disclosures of these references in their entireties are intended to be incorporated by reference into this application, in order to more fully describe the state of the art to which the invention pertains, except when these reference contradict the statements made herein.

What is claimed is:

1. An apparatus for measuring the effects of corrosion comprising:
    a container having a top, the container adapted to receive a first fluid and a second fluid within the container;
    a first holder assembly adapted to hold a first cylindrically shaped coupon and a second holder assembly adapted to hold a second cylindrically shaped coupon, each holder assembly having a cylindrical body, a bore, and a retainer, the retainer detachably connecting the respective coupon to the holder assembly;
    a shaft suspended from the top and extending into the container, the shaft adapted to pass through the bore of the first holder assembly and the second holder assembly, and to place the first coupon into contact with the first fluid and to place the second coupon into contact with the second fluid; and
    at least one sealing ring located adjacent to the first coupon and at least one sealing ring located adjacent to the second coupon, the first holder assembly urging the first coupon toward the respective sealing ring and the second holder assembly urging the second coupon toward the respective sealing ring independent of the shaft, the sealing rings preventing at least part of each coupon from contacting the first or second fluid.

2. The apparatus of claim 1, further comprising a third holder assembly adapted to hold a third cylindrically shaped coupon the third holder assembly having a cylindrical body and a bore;
    wherein the container is further adapted to receive a third fluid located within the container;
    wherein the shaft is further adapted to receive the third holder assembly and place the third coupon into contact with the third fluid; and
    at least one sealing ring is located adjacent to the third coupon, the third holder assembly urging the third coupon toward the respective sealing ring before the shaft passes through the bore of the third holder assembly.

3. The apparatus of claim 2, wherein
each holder assembly is adapted to hold at least three cylindrically shaped coupons; and
the first holder assembly is adapted to be substantially located in the first fluid, the first fluid creating a first phase, the second holder assembly is adapted to be substantially located in the second fluid, the second fluid creating a second phase, and the third holder assembly is adapted to be substantially located in the third fluid, the third fluid creating a third phase.

4. The apparatus of claim 1, the apparatus further comprising a motor attached to the shaft, operable to rotate the shaft.

5. The apparatus of claim 1, further comprising a first fluid and a second fluid, the first fluid creating a first phase and the second fluid creating a second phase;
wherein each of the holder assemblies is adapted to hold a plurality of coupons in a different phase; and
each of the holder assemblies comprise a first member having a stop ring and a threaded shaft connected to the stop ring and a second member having a stop ring and a threaded bore connected to the stop ring, the threaded bore threadingly engaging the threaded shaft to urge each of the plurality of coupon toward the respective adjacent sealing ring.

6. The apparatus of claim 5, wherein each of the plurality of holder assemblies is operable to be placed into a different fluid.

7. The apparatus of claim 5, wherein:
a third fluid is located in the container, the third fluid creating a third fluid phase;
the shaft is further adapted to receive a third holder assembly having a third coupon and place the third coupon into contact with the third fluid;
each of the first fluid, second fluid, and third fluid are selected from the group consisting essentially of oil, water, gas, and emulsions and mixtures of the same; and
wherein at least one of the first phase, second phase, or third phase comprises a corrosion inhibitor.

8. A method for measuring the effects of corrosion, the method comprising:
(a) weighing a first and second coupon of a first set of coupons to determine an initial first coupon weight and an initial second coupon weight;
(b) recording the initial first coupon weight and the initial second coupon weight;
(c) securing the first coupon from the first set of coupons on a first holder assembly;
(d) securing the second coupon from the first set of coupons on a second holder assembly;
(e) after steps (c) and (d), removably connecting each of the first and second holder assemblies, with respective coupons secured thereto, to a shaft;
(f) placing a first fluid and a second fluid in a vessel, the first fluid creating a first phase and the second fluid creating a second phase;
(g) adding a corrosion inhibitor to at least the first phase;
(h) placing the shaft in the vessel such that the first coupon is located in the first fluid and the second coupon is located in the second fluid;
(i) maintaining the first coupon within the first fluid for a pre-determined period of time;
(j) maintaining the second coupon within the second fluid for the pre-determined period of time;
(k) removing the first coupon and the second coupon from the shaft after the predetermined amount of time has lapsed;
(l) weighing the first and second coupons to determine a final first coupon weight and a final second coupon weight;
(m) recording the final first coupon weight and the final second coupon weight;
(n) determining the amount of material removed by corrosion from the first coupon by comparing the final first coupon weight with the initial first coupon weight; and
(o) determining the amount of material removed by corrosion from the second coupon by comparing the final second coupon weight with the initial second coupon weight.

9. The method of claim 8, wherein the holder assemblies each comprise a first member having a stop ring and a threaded shaft connected to the stop ring and a second member having a stop ring and a threaded bore connected to the stop ring, and steps (c) and (d) further comprise placing a sealing ring adjacent to each of the fist and second coupons then threadingly engaging the threaded bore with the threaded shaft to urge each of the first and second coupons toward the respective adjacent sealing ring.

10. The method of claim 8, further comprising pressurizing the vessel during a substantial portion of the predetermined amount of time.

11. The method of claim 8, further comprising rotating the shaft white the first and second coupons are in contact with the first and second fluid during at least a portion of the predetermined amount of time.

12. The method of claim 8, further comprising
installing at least one of the coupons from the first set of coupons on a third holder assembly;
attaching the third holder assembly to the shaft; and
maintaining the third holder assembly in contact with a third fluid in the vessel during the predetermined amount of time, the third fluid creating a third phase.

13. The method of claim 12, further comprising:
weighing a fourth coupon, a fifth coupon, and a sixth coupon of a second set of coupons to determine an initial fourth coupon weight, an initial fifth coupon weight, and an initial sixth coupon weight; and
attaching at least one coupon of the second set of coupons to each of the first, second, and third holders assemblies.

14. The method of claim 8, further comprising adding a corrosion inhibitor to at least the first phase.

15. The method of claim 8, wherein the first fluid is selected from the group consisting essentially of oil, water, gas, and emulsions and mixtures of the same.

16. The method of claim 8, further comprising placing at least one sealing ring adjacent to each of the coupons and wherein each of the holder assemblies urges the coupons on the respective holder assembly toward the respective sealing ring such that at least part of each coupon does not contact fluid.

17. The method of claim 8, wherein the first and second holder assemblies are separated by at least one spacer, the spacer being adapted to locate the first holder assembly substantially in the first fluid and the second holder assembly substantially in the second fluid for the predetermined amount of time.

18. An apparatus for measuring the effects of corrosion comprising:
a vessel having a body defining a vessel chamber and a lid;
a shaft suspended from the lid and located within the vessel chamber;
a first fluid and a second fluid located within the vessel chamber;

a first and second holder assembly, each holder assembly defining a bore, the shaft passing through the first holder assembly bore and the second holder assembly bore, such that the first holder assembly and second holder assembly are connected to the shaft;

a spacer located between the first and second holder assemblies, the spacer operable to maintain the first holder assembly a predetermined distance away from the second holder assembly;

a first and second coupon removably attached to the first holder assembly by an upper and lower retaining flange of the first holder assembly, the first and second coupon being in contact with the first fluid;

a third and fourth coupon removably attached to the second holder assembly by an upper and lower retaining flange of the second holder assembly, the third and fourth coupon being and in contact with the second fluid; and at least one sealing ring located between the first and second coupon, wherein the first holder assembly urges the first and second coupons toward the sealing ring independent of the shaft and the sealing ring prevents at least part of each coupon from contacting the first fluid.

19. The apparatus according to claim 18, wherein each coupon is further defined by a first and second sidewall, and wherein each sidewall of each coupon is substantially prevented from contacting fluid.

20. The apparatus according to claim 18, further comprising a motor located on the lid, operable to rotate the shaft.

21. The apparatus according to claim 18, further comprising:
a third fluid located within the vessel chamber; and
a fifth and sixth coupon located on a third holder assembly and in contact with the third fluid.

22. The apparatus according to claim 18, wherein the first coupon and second coupon are made of different materials.

* * * * *

UNITED STATES PATENT AND TRADEMARK OFFICE
CERTIFICATE OF CORRECTION

PATENT NO. : 8,408,053 B2
APPLICATION NO. : 12/786247
DATED : April 2, 2013
INVENTOR(S) : Sulaiman A. Al-Jutaily It is certified that error appears in the above-identified patent and that said Letters Patent is hereby corrected as shown below:

In the Claims:

Column 11, Claim 5, line 25, the claim language "coupon toward the respective adjacent sealing ring." should read --coupons toward the respective adjacent sealing ring.--

Column 12, Claim 9, line 19, the claim language "sealing ring adjacent to each of the fist and second coupons" should read --sealing ring adjacent to each of the first and second coupons--

Signed and Sealed this
Fourteenth Day of May, 2013

Teresa Stanek Rea
*Acting Director of the United States Patent and Trademark Office*